United States Patent [19]

Keuper

[11] Patent Number: 5,296,357
[45] Date of Patent: Mar. 22, 1994

[54] METHOD FOR THE DETECTION OF PLASMINOGEN ACTIVATORS, THEIR INHIBITORS OF STIMULATORS

[75] Inventor: Hermann Keuper, Wetter, Fed. Rep. of Germany

[73] Assignee: Behringwerke Aktiengesellschaft, Marburg, Fed. Rep. of Germany

[21] Appl. No.: 704,876

[22] Filed: May 23, 1991

[30] Foreign Application Priority Data

May 25, 1990 [DE] Fed. Rep. of Germany ....... 4016978

[51] Int. Cl.$^5$ .................. C12Q 1/37; C12N 9/68; A61K 37/547
[52] U.S. Cl. .................. 435/23; 435/217; 530/380; 424/94.63; 424/94.64
[58] Field of Search .............. 435/23, 217; 530/380; 424/94.64, 94.63; 436/69

[56] References Cited

U.S. PATENT DOCUMENTS

| 4,774,087 | 9/1988 | Wu | 424/94.64 |
| 5,057,414 | 10/1991 | Stief | 435/13 |
| 5,096,811 | 3/1992 | Hotchriss | 435/13 |

OTHER PUBLICATIONS

Drapier et al., Biochimie, 61, 463–471 (1979).
Kolde et al., Thrombosis and Haemostasis, 56, 155–159 (1986).
Machovich et al., Biochemistry, 28, 4517–4522 (1989).
Shi et al., The Journal of Biological Chemistry, 263, 17071–17076 (1988).
Chmielewska et al., Clinical Chemistry, 32, 482–485 (1986).

*Primary Examiner*—Michael G. Wityshyn
*Assistant Examiner*—Ralph Gitomer
*Attorney, Agent, or Firm*—Finnegan, Henderson, Farabow, Garrett & Dunner

[57] ABSTRACT

The invention relates to a method for the detection of the functional activity of plasminogen activators and of their inhibitors and stimulators in biological samples, and to reagents for this method.

8 Claims, 3 Drawing Sheets

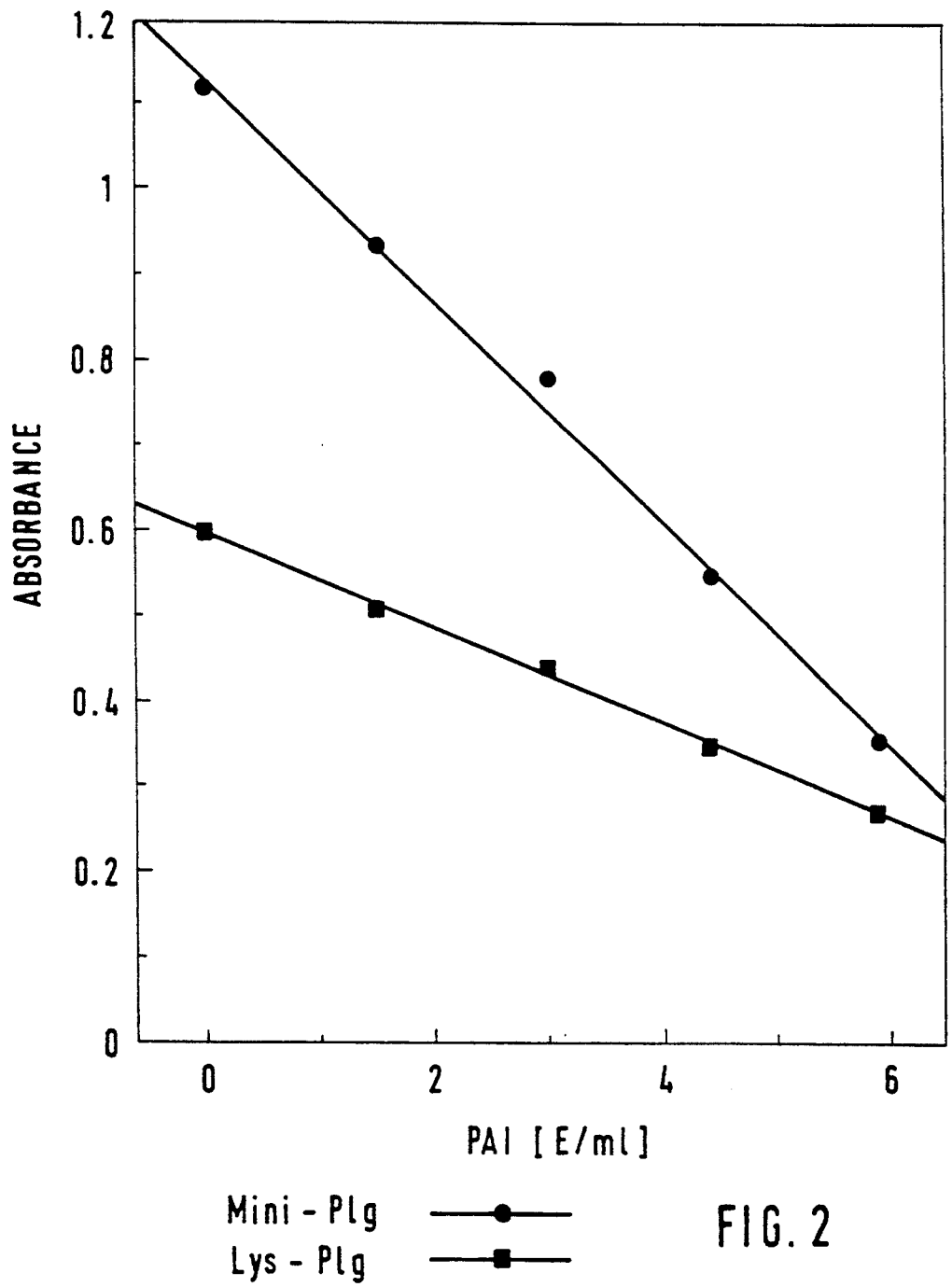

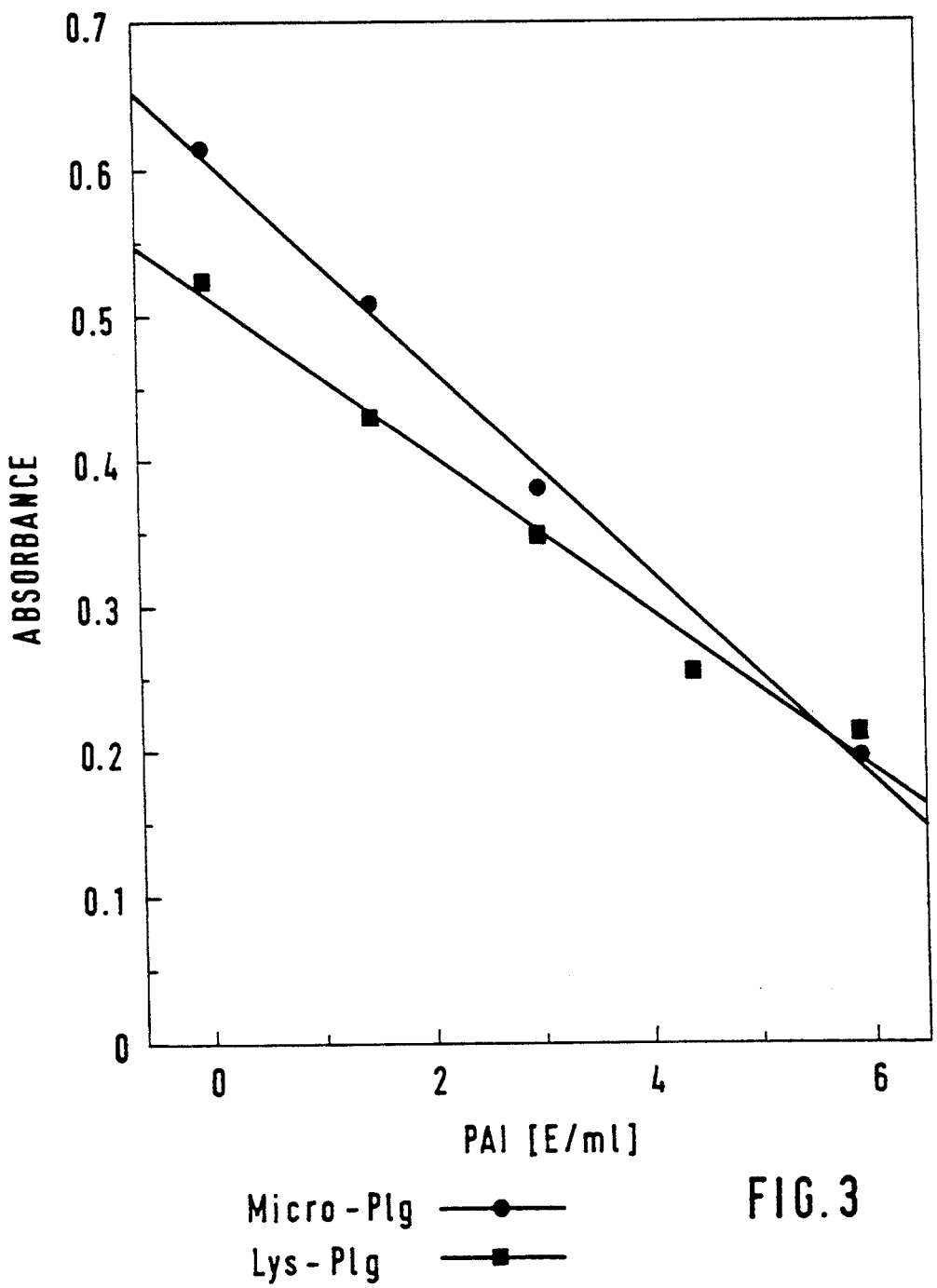

METHOD FOR THE DETECTION OF PLASMINOGEN ACTIVATORS, THEIR INHIBITORS OF STIMULATORS

The invention relates to a method for the detection of the functional activity of plasminogen activators and of their inhibitors and stimulators in biological samples, and to reagents for this method.

The functional determination of plasminogen activators (PA), their inhibitors (PAI) or stimulators in plasma is becoming increasingly important for routine clinical diagnosis. It is necessary for this purpose to develop rapid and sensitive assays which are able to detect the said proteins in concentrations of a few $\mu g/l$. In the case of PAI or PA stimulators (for example fibrin monomers and fibrin(ogen) degradation products for tPA), the plasma sample is normally mixed with a defined amount of PA and the remaining activity or stimulated activity thereof is measured.

A method has been disclosed (Drapier, J. D., Tenu, J. P., Lemaire, G., Petit, J. F., Biochimie 61 (1979) 463–471) in which the sensitivity has been increased by determining the activity of PA via the activation of the plasminogen, which has been added to the assay mixture, to plasmin. The resulting plasmin can then be detected, for example, with a chromogenic substrate. $Glu^1$-, $Lys^{78}$-plasminogen or a mixture of these plasminogen variants is employed in this method.

However, this method has a serious disadvantage in that plasma samples contain $\alpha_2$-antiplasmin which rapidly and irreversibly inhibits the resulting $Glu^1$- or $Lys^{78}$-plasmin. The interfering effect of the $\alpha_2$-antiplasmin is eliminated in the method by dilution and/or precipitation, which leads to complicated manipulation and excessively long times taken for the activity determination. Consequently, this method is little suited to routine diagnosis. Alternatively, $\alpha_2$-antiplasmin can be inactivated by oxidation, but this makes pipetting of an additional reagent necessary (DE 37 22 082). In addition, the use of oxidative inactivation of $\alpha_2$-antiplasmin is restricted to determination methods in which all essential components are markedly less sensitive to oxidation than is $\alpha_2$-antiplasmin.

The object on which the invention is based was thus to find a method for the functional determination of plasminogen activator activity and the modulation thereof by inhibitors or stimulators, which method is straightforward and reliable and can also be carried out in automatic analyzers.

BRIEF DESCRIPTION OF THE DRAWINGS

FIG. 2 is a graph depicting a comparison of Lys-Plasminogen and Mini-Plasminogen in the determination of PAI activity.

FIG. 3 is a graph depicting a comparison of Lys-Plasminogen and Micro-Plasminogen in the determination of PAI activity.

Figure 1:
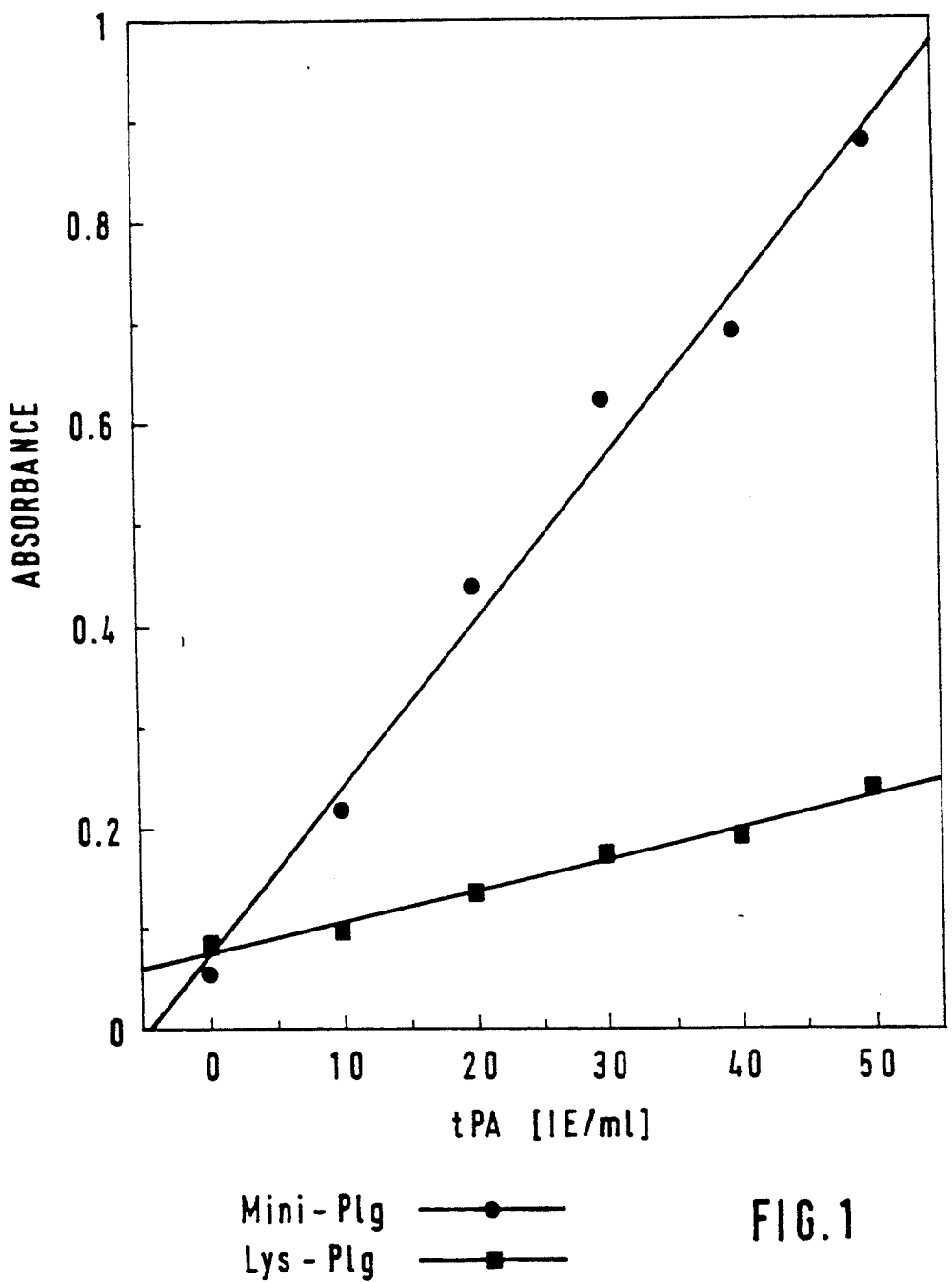
FIG. 1 is a graph depicting a comparison of Lys-Plasminogen and Mini-Plasminogen in the determination of tPA.

A method for the functional determination of plasminogen activator activity and the modification thereof by inhibitors or stimulators in body fluids is now proposed according to the invention, where the PA substrate employed is a plasminogen variant which, after activation to the corresponding plasmin variant, can be inhibited by $\alpha_2$-antiplasmin only slowly, if at all. The resulting plasmin or the plasmin variant is preferably detected with chromogenic substrates. Chromogenic plasmin substrates are known per se to the person skilled in the art (see, for example, KOLDE, H.-J. et al., Thrombosis and Haemostasis 56 (1986), pages 155–159).

Methods for the determination of functional plasminogen activator activity are known per se to the person skilled in the art (see, for example, DE 37 22 082).

A preferred method is one in which a sample of a biological material, preferably plasma, is incubated with a plasminogen variant in an amount of 0.05–50 $\mu mol/l$, particularly preferably 0.1–5 $\mu mol/l$, preferably with mini- and micro-plasminogen and with a chromogenic plasmin substrate (0.01–10 mmol/l), preferably HD-Nva-CHA-Lys-pNA or HD-Val-Leu-Lys-pNA. To determine inhibitors or stimulators of PA, it is possible additionally to add PAs such as, for example, tPA or urokinase. The evaluation is preferably carried out by comparing the absorbance measured in the absorption medium of the liberated chromophore, or the change in absorbance per unit time with a calibration plot.

The embodiments indicated in the examples are very particularly preferred.

The plasminogen variants used in the method according to the invention are those which, after activation to the corresponding plasmin variant, continue to show plasmin activity and are inhibited by $\alpha_2$-antiplasmin only slowly, if at all.

Particularly preferred variants in this connection are those in which the kringle domains 1–4 are partially or completely absent, and very particularly preferred are mini-plasminogen ($Val^{442}$-plasminogen) and micro-plasminogen ($Lys^{530}$-plasminogen) in the method according to the invention. These plasminogen variants can be prepared by chemical, enzymatic or genetic engineering methods known per se to the person skilled in the art (see, for example, B. R. Machovich, W. G. Owen, Biochemistry 28 (1989) 4517–4522, mini-plasminogen; G.-Y. Shi, H.-L. Wu, J. Biol. Chem. 263 (1988) 17071–17075, micro-plasminogen).

The plasminogen variants according to the invention can also be generated directly in the assay mixture by methods known per se to the person skilled in the art.

The use of the plasminogen variants according to the invention makes it unnecessary to reduce the concentration of or inactivate $\alpha_2$-antiplasmin, and the determination methods can be considerably simplified. Methods for detecting and for quantifying plasmin are known per se to the person skilled in the art. The determination is preferably carried out with the aid of chromogenic substrates such as, for example, HD-Nva-CHA-Lys-pNA or HD-Val-Leu-Lys-pNA.

The determination can be carried out kinetically or as an endpoint method. The determination can take place at 10°–40° C., preferably at 20°–40° C., very particularly preferably at 37° C.

Compared with the known state of the art (DE 37 22 082), the method according to the invention is distinguished by its simplicity and sensitivity (see FIG. 1).

The examples which follow serve to illustrate the method according to the invention and should by no means be regarded as restrictive.

EXAMPLE 1

Comparison of Lys-plasminogen and mini-plasminogen in the determination of tPA activity 45 µl of a normal plasma pool were mixed with 50 µl of tPA in a concentration of 0–50 IU/ml in HEPPS buffer (50 mM N-(2-hydrozyethyl)piperzine-N'-3-propanesulfonic acid, 0.3% Triton X-100, pH 8.4) and 5 µl of fibrin monomers (0.8 g/l in 1M KBr). Subsequently 100 µl of Lys-plasminogen (2.3 µM in HEPPS buffer) or 100 µl of mini-plasminogen (1.1 µM in HEPPS buffer) and 800 µl of plasmin substrate (HD-norvalyl-cyclohexylalanyl-lysyl-p-nitroanilide, 0.19 mmol/l in HEPPS buffer) were added. After incubation at 37° C. for 30 min, the reaction was stopped with 200 µl of 20% acetic acid. The extinction at 405 nm of the liberated p-nitroaniline was measured with water as reference. The measured extinctions are plotted against the activity of the tPA introduced in FIG. 1. There is a linear relation for both plasminogen variants, but the slope of the curves, and thus the sensitivity, is more than 5 times higher for mini-plasminogen than on use of Lys-plasminogen, which moreover was employed in more than twice the concentration.

EXAMPLE 2

Comparison of Lys-plasminogen and mini-plasminogen in the determination of PAI activity Plasma samples with predefined PAI activities were prepared by mixing the PAI standards S1 (0 U/ml) and S2 (5.9 U/ml) from the Berichrom® PAI assay kit from Behringweke AG. 25 µl of the plasma sample were incubated at 37° C. for 5 min with 50 µl of urokinase in a concentration of 5 U/ml in tris buffer (100 mM TRIS/HCl, 100 mM NaCl, 1% Haemacel® (Behringwerke), 0.1% Triton X-100, pH 8.4). Subsequently 100 µl of mini-plasminogen (6.3 µm in TRIS buffer) were added and incubation was again carried out at 37° C. for 5 min. After addition of 250 µl of plasmin substrate (0.6 mM in 600 mM NaCl/50 mM TRIS/pH 8.4) and renewed incubation (37° C. for 5 min), the reaction was stopped with 50 µl of 50% acetic acid. The extinction at 405 nm of the liberated p-nitroaniline was measured; for the reference, TRIS buffer was added to the sample in place of urokinase. For comparison, a PAI activity assay was carried out with the Behringwerke AG reagents (Berichrom® PAI) on the same samples. The assay takes place essentially as described above; Lys-plasminogen (7.3 µM) is used in place of mini-plasminogen, and chloramin T must be added together with the plasminogen for the oxidative inactivation of interfering $\alpha_2$-antiplasmin in the plasma sample. The measured absorbances are plotted against the PAI activity introduced in FIG. 2. there is a linear relation for both plasminogen variants. In contrast to the experiment with Lys-plasminogen, however, the $\alpha_2$-antiplasmin contained in the sample had not been inactivated with chloramine T in the case of measurement of the PAI activity with mini-plasminogen. Nevertheless, the gradient of the lines, and thus the sensitivity, is more than twice as high in the case of mini-plasminogen than when Lys-plasminogen was used. If no chloramine T is added when Lys-plasminogen is used, it is not possible to carry out functional PAI determinations under these conditions.

EXAMPLE 3

Comparison of Lys-plasminogen and micro-plasminogen in the determination of PAI activity The experiment described in Example 2 was repeated with 13 µM micro-plasminogen in place of mini-plasminogen. The "Berichrom® PAI" assay with inactivation of $\alpha_2$-antiplasmin by chloramine T was likewise carried out as reference method. It is evident from FIG. 3 that oxidative inactivation of $\alpha_2$-antiplasmin is superfluous when micro-plasminogen is used too.

I claim:

1. A method for the functional determination of plasminogen activator (PA) activity and the modulation thereof in body fluids, comprising the steps of:
   a) incubating a sample of a biological material with a plasminogen activator substrate in the absence of a methionine oxidizing agent; and
   b) determining the resulting plasmin variant by means of a chromogenic plasmin substrate,
   wherein said plasminogen activator substrate is a plasminogen variant with kringle domains 1–4 partially or completely absent.

2. The method as claimed in claim 1, further comprising adding tPA or urokinase for the determination of inhibitors of PA activity.

3. The method of claim 2, wherein the tPA or urokinase are added for determining stimulators of PA activity.

4. The method as claimed in claim 1, wherein the plasminogen variant is mini-plasminogen or micro-plasminogen.

5. The method of claim 4, wherein the plasminogen variant is microplasminogen.

6. The method as claimed in claim 1, wherein a sample of a biological material in body fluid at a concentration of 0.5–50 µmol/l is incubated with said plasminogen variant, and with a solution at 0.01–10 mmol/l of the chromogenic substrate HD-Nva-CHA-Lys-pNA and the plasmin variant is determined by comparing the measured absorption of change of absorbance with a calibration curve.

7. The method as claimed in claim 6, wherein the chromogenic substrate is HD-Val-Leu-Lys-pNA.

8. The method of claim 6, wherein the biological material is plasma.

* * * * *